United States Patent [19]

Farng et al.

[11] Patent Number: 5,006,270

[45] Date of Patent: Apr. 9, 1991

[54] MIXED RESORCINOL-HYDROXYESTER BORATES AS ANTIOXIDANTS

[75] Inventors: Liehpao O. Farng, Lawrenceville; Andrew G. Horodysky, Cherry Hill, both of N.J.

[73] Assignee: Mobil Oil Corporation, New York, N.Y.

[21] Appl. No.: 346,033

[22] Filed: May 1, 1989

[51] Int. Cl.$^5$ .............................................. C10M 105/16
[52] U.S. Cl. ................................. 252/42.7; 252/52 R; 252/56 R; 558/294; 558/296
[58] Field of Search ................ 252/42.7, 49.6, 515 A, 252/42.7, 49.6, 49.7, 52 R, 56 R; 558/294, 296

[56] References Cited

U.S. PATENT DOCUMENTS

| | | | |
|---|---|---|---|
| 3,533,945 | 10/1970 | Vogel | 252/49.6 |
| 4,240,970 | 12/1980 | Chibnik | 548/520 |
| 4,295,983 | 10/1981 | Papay | 252/49.6 |
| 4,370,248 | 1/1983 | Horodysky | 252/49.6 |
| 4,568,472 | 2/1986 | Horodysky | 252/49.6 |
| 4,828,740 | 5/1989 | Farng | 558/296 |

*Primary Examiner*—William R. Dixon, Jr.
*Assistant Examiner*—James M. Hunter, Jr.
*Attorney, Agent, or Firm*—Alexander J. McKillop; Charles J. Speciale; Howard M. Flournoy

[57] ABSTRACT

Mixed resorcinol-hydroxyester borates have been found to be effective multifunctional additives when incorporated into various lubricating media.

17 Claims, No Drawings

MIXED RESORCINOL-HYDROXYESTER BORATES AS ANTIOXIDANTS

This application is related to copending application, Ser. No. 078,949, filed Jul. 29, 1987, and entitled MIXED HYDROQUINONE-HYDROXYESTER BORATES AS ANTIOXIDANTS and now U.S. Pat. No. 4,828,740. This application is also related to Ser. No. 346,031, filed May 1, 1989 and entitled MIXED ALKOXYLATED ALCOHOL-HYDROQUINONE/RESORCINOL BORATES-ANTIOXIDANTS.

BACKGROUND OF THE INVENTION

This application is directed to lubricant compositions containing small additive concentrations of mixed hydroxyaryl-hydroxyester borates having excellent multifuntional/antioxidant activity.

The use of hydroxyaryls have been well known for their antioxidant properties in a variety of petroleum and non-petroleum products. The use of borates have found extensive application in such diverse areas as grease additives, brake and hydraulic fluids, and fuel and combustion additives. The use of hydroxyesters have been widely reported as having beneficial multifunctional characteristics in a variety of fuel and lubricant applications.

U.S. Pat. Nos. 4,655,948 and 4,781,850 relate to grease compositions containing borated catechol (ortho-dihydroxybenzene, e.g., catechol-alcohol borates useful in reducing dropping point.

U.S. Pat. Nos. 4,594,171 and 4,568,472 discloses the use of borated additive compounds such as borated hydroxyesters in lubricant compositions. U.S. Pat. No. 4,654,082 discloses the use of hydroquinones as an antioxidant in ink compositions. U.S. Pat. No. 4,223,735 discloses the use of of hydroquinones as an oxidation inhibitor in a method of producing petroleum.

U.S. Pat. No. 4,240,970 in one embodiment is directed to the use of (1) the product of reaction between an alkenylsuccinic acid, ester or anhydride and a hydroxyaromatic (hydroxyaryl) compound and (2) the product of reaction of (1) and an amine as detergents in lubricant compositions.

Lubricant compositions containing small additive concentrations of mixed hydroquinone-hydroxyester borates such as hydroquinone-glycerol monooleate borates as disclosed in Ser. No. 078,949, possess excellent antioxidant activity.

It has now been found that the use of these novel mixed hydroxyaryl-hydroxyester borates provide exceptional antioxidant and corrosion inhibiting activity with the potential for antifatigue, friction reducing, antirust and high temperature stabilizing properties. These novel borates are also highly useful not only in oils of lubrication viscosity but also in solid lubricants such as greases.

SUMMARY OF THE INVENTION

Hydroxyaryl or hydroxyaromatic-hydroxyester borates also possess excellent antioxidant activity when incorporated into lubricant compositions. Typical hydroxyaryl compounds include resorcinol and alkyl-substituted resorcinols.

Although not wishing to be bound by a particular theory both the hydroxyaryl moiety and the borate ester are believed to provide the basis for synergistic antioxidant activity, the hydroxyester is believed to contribute additional antirust and/or friction reducing properties to the additives. These beneficial properties are believed to be enhanced as a result of this novel internal synergism. This internal synergism concept is believed to be applicable to similar structures containing hydroxyaryl, borate ester and hydroxyester (preferably diol containing) moieties within the same molecule. The products disclosed herein also show good compatibility when used in the presence of other additives in the lubricant compositions.

DESCRIPTION OF PREFERRED EMBODIMENTS

Resorcinol is for example co-borated with glycerol monooleate 60% glycerol monooleate, 40% glycerol dioleate) to form mixed borate esters having the structure, as generally described below:

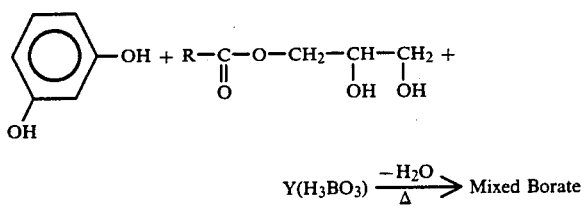

where R is $C_8$–$C_{20}$ hydrocarbyl and Y is the boronating agent.

Other appropriate hydroxyaryl compounds can be generally described as:

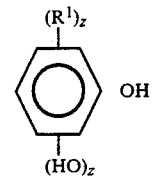

where $R^1$ is hydrocarbyl having from 1 to about 300 carbon atoms, z is from 1 to 5.

Other appropriate hydroxyesters can be more generally described as:

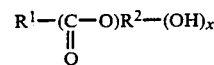

or

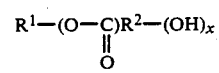

where x is 1 or 2 and where $R^1$ and $R^2$ are each independently $C_1$–$C_{20}$ hydrocarbyl.

The generalized structure of the hydroxyesters, useful herein before boration, is exemplified by the following:

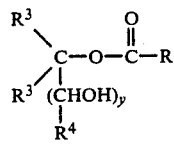

Where $R^3 = CH_2OH$, $CH_3$ or H
$R^4 = CH_2OH$, H, or $CR^2 OCOR$
y = 1 to 5
R and $R^2$ are each independently selected from $C_8$ to about $C_{20}$ hydrocarbyl.

The hydroxy esters must contain at least one free hydroxyl group but may contain two or more. The hydroxy esters may also contain one ester group (as is glycerol monooleate) or more (as in glycerol dioleate). The esters can be used in pure form, or preferably in mixtures such as mixtures of glycerol mono- and dioleate. R is a hydrocarbyl group having from about 8 to about 20 carbon atoms and said hydrocarbyl moiety may be alkyl, straight or branched, cyclic or substituted; and may contain one or more double bonds, halogen or one or more sulfur atoms or aromatic rings and y is 1 to about 5. The hydroxy esters may be made by the reaction of polyhydroxy alcohols with organic acids where glycerol and oleic acid are used in the preparation of glycerol monooleate. Thioglycerol hydroxyesters can also be used.

Sorbitan hydroxyesters and hydroxyesters prepared from trimethylolpropane and pentaerythritol are also useful, e.g., sorbitan monooleate, trimethylolpropane monooleate, trimethylolpropane dioleate, pentaerythritol dioleate monolaurate and the like.

The term "hydroxyaromatic compound" is meant to include phenol, naphthol, anthrol, catechol, resorcinol and the like, as well as the high molecular weight members thereof. Representative high molecular weight alkyl-substituted hydroxyaromatic compounds contemplated include polypropenyl-, polybutenyl- and polyamylenephenol and similarly substituted phenols. In addition to the substituted phenol, high molecular weight alkyl-substituted compounds of resorcinal catechol, cresol, xylenol, amyl phenol, hydroxydiphenyl, benzylphenol, phenylethylphenol, methylhydroxydiphenyl, alpha and beta naphthol, alpha and beta methylnaphthol, tolylnaphthol, xylynaphthol, benzylnapthol, anthrol, phenylmethylnaphthol, phenanthrol, chlorophenol, and the like may be used. Particularly preferred are resorcinol and alkyl substituted resorcinols.

It is in general contemplated that the alkyl group will have from 1 to 300 carbon atoms. Preferably, the alkyl will contain from 1 to 50 carbon atoms. The alkyl group may be derived from a simple alkene or from a polymer or copolymer of such alkenes. The alkene may be selected from 1-octene, 1-decene, 1-dodecene and the like. The polymers or copolymers may be made from these or from other olefins such as ethene, propene, butene, isobutene and the like.

The borated derivatives are conveniently produced by the reaction of the selected mixture of compounds with, for example, boric acid, in the presence of a suitable solvent or solvents at temperatures ranging from about 80° C. to about 280° C. Specific reactor conditions and molar equivalents vary with the various reactants and can be readily determined by one of ordinary skill in the art. Besides direct treatment with boric acid other boration procedures several of which are well known in the art can be used, for example, transesterification with a trialkyl borate such as tributyl borate. Accordingly, metaborates, triaklyl borates or any other suitable boronating agent may be employed.

In any event, the boration procedure generally adopted is conveniently a one-pot, one-step process. The resulting borated mixed materials are much more effective as antioxidant/friction reducing lubricant additives than their non-borated counterparts or physical mixtures of the individual borated materials. The borated mixed materials possess antioxidant and corrosion inhibiting properties not generally found in the non-borated material and are superior to equivalent physical mixtures of the individual borated materials. The higher molecular weight borated mixtures also appear to be relatively resistant to hydrolysis and retain their multifunctional characteristics even after being in the presence of water at elevated temperatures.

An excess of one reagent or another can be used. Molar quantities, less than molar quantities, or more than molar quantities of boronating agent can be used. The molar rating of the respective reactants may, however, be conveniently generalized as follows: 1–20: 0.1–10: 0.1–5 and preferably 1:1:1 of hydroxyester to hydroxyaryl compounds to boronating substance.

EXAMPLES

EXAMPLE 1

Approximately 33 g resorcinol, 55.6 g boric acid and 202.8 g of triethoxylated mixed dodecanol-pentadecanol (commercially obtained from Shell Chemical Company, as Neodol 25-3) and 200 ml toluene were mixed in a reactor equipped with heater, stirrer and Dean-Stark trap. The reactants were initially heated at about 90° C. for one hour, then at 115° C. for six hours. When water evolution ceased 26 g water had been azeotropically collected. The solvent was subsequently removed by vacuum distillation at about 125° C. and the borated product was filtered through diatomaceous eath (257 g).

EXAMPLE 2

Approximately 35 g resorcinol, 55.6 g boric acid, 151.2 g Neodol 25-3, 100 g glycerol monoeleate, and 200 ml toluene were mixed and reacted as described in Example 1. 31 g Water was azeotropically removed as side product. The borated product was filtered trhough diatomaceous eath and approximately 308 g viscous, brown fluid was recovered.

EXAMPLE 3

Resorcinol-glycerol monoleate mixed borates

Approximately 22.8 g resorcinol, 150 g glycerol monoleate (commercially obtained for Emery Chemical Company), 20.6 g boric acid, and 150 ml toluene were mixed in a reactor equipped with heater, stirrer, and Dean-Stark trap. The reactants were heated at 90° C. for an hour, then at 110° to 115° C. for three hours, during which 10 g water was azeotropically collected. Thereafter, the volatiles were removed by distillation at reduced pressure and approximately 178.6 g of product was recovered as a brownish fluid.

EVALUATION OF PRODUCT

The product of the Examples were blended into synthetic ester-based lubricants and evaluated for antioxidant preformance using the Differential Scanning Caloimetry test method (DSC). DSC is reputedly the most widely used thermal analysis technique in the lubricant laboratory. In DSC the environment of a sample is either heated or cooled at a linear rate (i.e., the "scanning" part). During this scan, the energy uptake or release by the sample is compared quantitatively (i.e., calorimetrically) with an inert material (i.e., differentially). This measurement (and its display by a recording device) of the sample's basic thermodynamic properties is related to quality assurance parameters.

It is used herein to determine the onset of oxidation of the test material. For more complete information, please refer to *SAE Technical Paper Series*, No. 801383, "Characterization of Lubricating Oils by Differential Scanning Calorimetry," by Walker et al., Oct. 20–23, 1980, and to the *Journal of the Institute of Petroleum*, Vol. 57, No. 558, November 1971, pages 355-358, "The Characterization of Lube Oils and Fuel Oils by DSC Analysis," by F. Noel, Imperial Oil Enterprises Ltd, Ontario, Canada) which was part of a presentation made at the ASTM D-2 Symposium in Dallas, Tex., Dec. 7, 1970.

TABLE

| DSC (Differential Scanning Calorimetry Test) (Equilibrate at 30° C. and ramp at 10° C./Min until 300° C. under atmospheric pressure) | |
| --- | --- |
| Example No. | Oxidation Onset Temperature |
| Synthetic ester base oil | 192.9° C. |
| 2% of Example 1 in above base oil | 253.9° C. |
| 2% of Example 2 in above base oil | 262.8° C. |
| 2% of Example 3 in above base oil | 252.1° C. |

As can be seen from the data in the Table, the mixed alkoxylated alcohol-resorcinol borates exhibit significant antioxidant properties by improving the thermal-/oxidative stability of the test lubricant, by as much as about 60° to 70° C.

The products of this invention show very good antioxidant activity as evidenced by the increased onset of oxidation of the examples in accordance with the invention as shown in the Table. The products of this invention when used in premium quality automotive and industrial lubricants will significantly enhance stability and extend service life. These multifunctional additives are ashless and do not contain any potentially undesirable metals or chlorine. They can be commercially made by an economically favorable process which could be readily implemented using known technology in existing equipment.

The products of this invention show very good antioxidant activity as evidenced by the increased onset of oxidation of the examples in accordance with the invention as shown in the Table. The products of this invention when used in premium quality automotive and industrial lubricants will significantly enhance stability and extend service life. These multifunctional additives are ashless and do not contain any potentially undesirable metals or chlorine. They can be commercially made by an economically favorable process which could be readily implemented using known technology in existing equipment.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

We claim:

1. A composition comprising a major proportion of an oil of lubricating viscosity or grease or other solid lubricant prepared therefrom and a minor amount of a multifunctional friction reducing, antirust and antioxidant additive selected from mixed hydroxyaryl-hydroxyester borates and wherein said additive is prepared in reactions as generally described below:

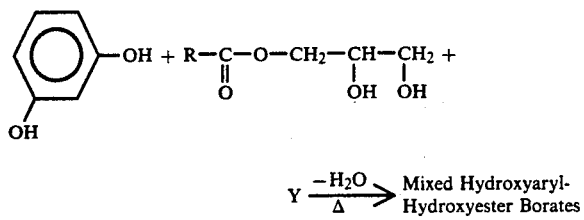

at temperatures varying from 80° to 280° C. in molar ratios of hydroxyester to hydroxyaryl to boronating agent of from about 1–20:1.0–10:0.1–5 and where R is $C_8$ to about $C_{20}$ hydrocarbyl and Y is said boronating agent and is selected from the group consisting of boric acid, metaborates and trialkyl borates.

2. The composition of claim 1 wherein said hydroxyester is a mixture of glycerol monooleate and glycerol dioleate.

3. The composition of claim 2 wherein resorcinol and said hydroxyesters are reacted with boric acid.

4. The composition of claim 1 wherein resorcinol and said hydroxyesters are reacted with boric acid.

5. The composition of claim 1 wherein said hydroxyester is glycerol monooleate.

6. The composition of claim 1 wherein said hydroxyester is glycerol dioleate.

7. The composition of claim 1 wherein said oil is selected from mineral oils synthetic oils and mixtures thereof.

8. The composition of claim 1 wherein said oil is a synthetic oil.

9. The composition of claim 1 wherein said oil is a mineral oil.

10. The composition of claim 1 wherein said oil is a mixture of synthetic and mineral oils.

11. The composition of claim 1 wherein said major proportion comprises a grease.

12. An additive product prepared by reacting mixed resorcinol hydroxyester with a boronating agent in less than, more than or molar amounts of hydroxyester and boronating agent under temperatures varying from 80° to about 280° C. in the reaction generally described below:

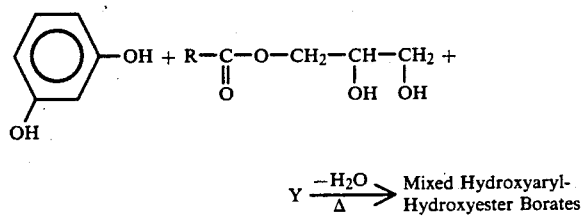

where R is $C_8$–$C_{20}$ hydrocarbyl and Y is said boronating agent selected from the group consisting of boric acid, metaborates, and trialkyl borates.

13. The product of claim 12 wherein the hydroxyester before boration has the following general structural formula:

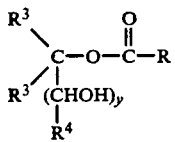

Wherein $R^3$ is $CH_2OH$, $CH_3$ or $H$; $R^4$ is $CH_2OH$, $H$, or $CR^2 OCOR$; $y$ is 1 to 5; $R$ and $R^2$ are each independently selected from $C_8$ to about $C_{20}$ hydrocarbyl.

14. The product of claim 13 wherein the hydroxyester is selected from glycerol monooleate, glycerol dioleate and a mixture of glycerol monooleate, and glycerol dioleate.

15. The product of claim 14 wherein the hydroxyester is glycerol monooleate.

16. The product of claim 14 wherein the hydroxyester is glycerol dioleate.

17. The additive product of claim 12 wherein the reactants are resorcinol, a mixture of monooleated glycerol and dioleated glycerol and boric acid.

* * * * *